United States Patent [19]

Della Bella et al.

[11] Patent Number: 4,918,095
[45] Date of Patent: Apr. 17, 1990

[54] COMPOSITIONS WITH ANTIBIOTIC ACTIVITY AND THEIR USE

[75] Inventors: Davide Della Bella; Giancarlo Jommi; Mario Fantucci, all of Milan; Dario Chiarino, Monza, all of Italy

[73] Assignee: Zambon S.p.A., Vicenza, Italy

[21] Appl. No.: 135,041

[22] Filed: Dec. 18, 1987

[30] Foreign Application Priority Data

Dec. 23, 1986 [IT] Italy .................. 22826 A/86

[51] Int. Cl.$^4$ .................. C07D 207/02; C07C 103/58
[52] U.S. Cl. .................. 514/423; 514/627; 514/518; 514/533; 514/534; 514/548; 514/552; 514/551; 514/550; 514/546; 564/207; 260/407; 548/531; 560/39; 560/40; 560/61; 560/85
[58] Field of Search .............. 564/207; 514/627, 533, 514/534, 548, 552, 551, 550, 546, 423, 518; 260/404; 560/39, 40, 61, 85, 105, 106, 153, 169, 170, 171, 186, 187, 196, 227, 250; 548/531

[56] References Cited

U.S. PATENT DOCUMENTS

| | | | |
|---|---|---|---|
| 2,717,268 | 9/1955 | Rebstock et al. | 564/212 |
| 2,727,070 | 12/1955 | Jacob | 564/213 |
| 2,727,071 | 12/1955 | Jacob et al. | 564/213 |
| 2,759,927 | 8/1956 | Suter | 564/207 |
| 2,759,970 | 8/1956 | Suter | 564/212 |
| 2,759,971 | 8/1956 | Cutler et al. | 564/219 |
| 2,759,972 | 8/1956 | Suter | 564/207 |
| 2,776,992 | 1/1957 | Gregory | 564/212 |
| 2,876,261 | 3/1959 | Jacob | 564/213 |
| 3,012,073 | 12/1961 | Gregory | 564/212 |
| 4,235,892 | 11/1980 | Nagabhushan | 514/626 |

Primary Examiner—Amelia Burgess Yarbrough
Assistant Examiner—Helene Kirschner
Attorney, Agent, or Firm—Stevens, Davis, Miller & Mosher

[57] ABSTRACT

The compound N-[(1S,2R)-fluoromethyl-2-hydroxy-2-(4-methylsulphonyl-phenyl)-ethyl]-2-propenamide and the derivatives thereof in which the hydroxy in 2 position is esterified by a mono or dicarboxylic acid or by an aminoacid are described.

Such compounds have antibiotic activity and are useful in human and veterinary therapy.

4 Claims, No Drawings

COMPOSITIONS WITH ANTIBIOTIC ACTIVITY AND THEIR USE

The present invention relates to compounds with antibiotic activity and, more particularly, it relates to the compound N-[(1S,2R)-1-fluoromethyl-2-hydroxy-2-(4-methylsulphonyl-phenyl)-ethyl]-2-propenamide and its prodrugs, its use in human and veterinary therapy and pharmaceutical preparations containing them.

Some compounds with antibiotic activity present on the market, contain the basic structure of N-dichloroacetyl-1-phenyl-2-amino-1,3-propanediol.

They are the compound known as Chloramphenicol (Merck Index, X Edition, No. 2035, page 289) in which the substituent on the phenyl is a nitro group in 4 position and the compound known as Thiamphenicol (Merck Index, X Edition, No. 9140, page 1332) in which the substituent on the phenyl is a methylsulphonyl group in 4 position.

Chloramphenicol, because of undesired side effects, is now used only in particular cases, while Thiamphenicol continues to be used both in human and veterinary therapy.

In European Patent No. 14 437 (Schering Corporation) some compounds with antibiotic activity have been described among which there are the analogous of Chloramphenicol and Thiamphenicol with the primary hydroxy group replaced by a fluorine atom.

The above mentioned compounds can be collected in the following general formula.

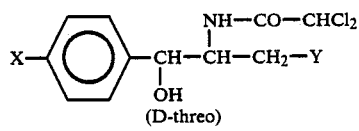

wherein:
I-A (X=NO₂, Y=OH)=Chloramphenicol
I-B (X=CH₃SO₂, Y=OH)=Thiamphenicol
I-C (X=NO₂, Y=F)=Compound according to EP 14 437
I-D (X=CH₃SO₂, Y=F)=Compound according to EP 14 437

The substitution of dichloroacetyl group in compounds I-A and I-B with different acyl groups was already described in literature [P. S. Ringrose and R. W. Lambert, Biochimica et Biophysica Acta, 299 (1973), 374–384].

Every described substitution, however, gave compounds with an antibiotic acitivity at least 7-8 times lower than that of the parent compounds (I-A and I-B).

Particularly one of the less active derivative was the compound with an acryloyl group instead of dichloroacetyl group.

In table 1 at page 378 of the above mentioned article, in fact, it is reported that the compound which differs from Chloramphenicol for an acryloyl radical on the amino group instead of a dichloroacetyl radical (compound I in the table) has an antibiotic activity, expressed as minimum growth inhibitory concentration (MGIC), 7.5 times lower than that of Chloramphenicol, and the analogous derivative of Thiamphenicol (compound XI in the table) is 22.5 times less active than Thiamphenicol.

We have now surprisingly found, and they are the object of the present invention, the compounds of formula

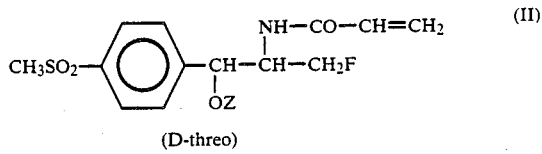

wherein:

Z represents a hydrogen atom or represents an optionally substituted acyl group derived from a saturated or unsaturated aliphatic, aromatic or arylaliphatic carboxylic acid having up to 16 carbon atoms, from an aliphatic or aromatic dicarboxylic acid having up to 12 carbon atoms, or from a natural aminoacid;

and, when Z is an acyl of a dicarboxylic acid or of an amino-acid, the corresponding pharmaceutically acceptable salts with bases or with acids respectively.

The compounds of formula II are endowed with antibiotic acitivity and they can be used in human and veterinary therapy.

The compound N-[1S,2R)-1-fluoromethyl-2-hydroxy-2-(4-methylsulphonyl-phenyl)-ethyl]-2-propenamide (II, Z=H) which may be also indicated as D-(threo)-1-(4-methylsulphonyl-phenyl)-2-acrylamido-3-fluoro-1-propanol (from now on indicated as II-A) is the responsible of the antibiotic activity.

The esters of formula II (Z different from H) represent derivatives of compound II-A useful for modifying the chemical-physical characteristics in relation to specific requirements in formulation or administration.

Among the esters of formula II we can mention:

(a) the esters with pharmaceutically acceptable monocarboxylic acids selected, for instance, among acetic, propionic, butyric, isobutyric, pentanoic, hexanoic, tert.butylacetic, octanoic, decanoic, lauric, palmitic, phenlacetic, phenoxyacetic, glyceric, 2-phenyl-propionic, methoxyacetic, trifluoroacetic, benzoic, 3,5-dimethyl-benzoic, cinnamic and sorbic acid;

(b) the monoesters of pharmaceutically acceptable dicarboxylic acids selected, for instance, among tartaric, succinic, phthalic and hydroxy-phthalic acid and the corresponding salts in which the not-esterified carboxy group is salified with an inorganic base (sodium, potassium and calcium salts) or with an organic base such as 2-amino-2,2-dihydroxymethyl-ethanol and basic aminoacids;

(c) the esters with natural aminoacids selected, for instance, among glycine, alanine, lysine, arginine, phenylalanine, leucine, isoleucine, serine, threonine, proline, cysteine, N-acetylcysteine and the corresponding salts in which the amino group of the aminoacid makes an addition salt with an inorganic acid selected, for instance, among hydrochloric, hydrobromic and sulphuric acid or with an organic acid selected, for instance, between acetic and methanesulphonic acid.

The preparation of the compounds of formula II is preferably carried out by preparing, first, the compound of formula II-A and, if desired, by performing subsequently the esterification and the optional salification.

Compound II-A can be prepared according to different alternative routes which, generally, comprise the following steps starting from D-(threo)-1-(4-methylthiophenyl)-2-amino-1,3-propanediol (known as Thiomicamine):

replacement of the primary hydroxy group by fluorine oxidation of the methylthio group to methylsulphonyl acylation of the amino group with acrylic acid or a reactive derivative or a precursor thereof.

These reactions may be carried out according to various procedures and following a different order.

It is suitable to protect the secondary hydroxy group and the amino group during the fluorination reaction.

Said protection may be achieved simultaneously by preparing cyclic intermediates like for example oxazoline derivatives.

The acylation may be carried out as the last step of the process on the deprotected fluoromethyl-derivative or the acyl group (or a precursor thereof) may be introduce in the molecule as protecting group prior to the fluorination reaction.

Accordingly one of these processes comprise the N-acylation of the compound D-(threo)-1-(4-methylsulphonyl)-2-amino-3-fluoro-1-propanol (described in European Patent No. 14 437) with a derivative of acrylic acid such as an acryloyl halide, preferably chloride, a reactive ester or an anhydride.

The reaction is carried out in an inert solvent, optionally in the presence of a base and at a temperature between −20° C. and the boiling temperature of the reaction mixture.

When the acylating agent is acryloyl chloride the temperature is preferably between 0° C. and room temperature.

Other alternatively processes which also start from Thiomicamine (1), an intermediate compound in the synthesis of Thiamphenicol, are reported in the following schemes.

Scheme 1

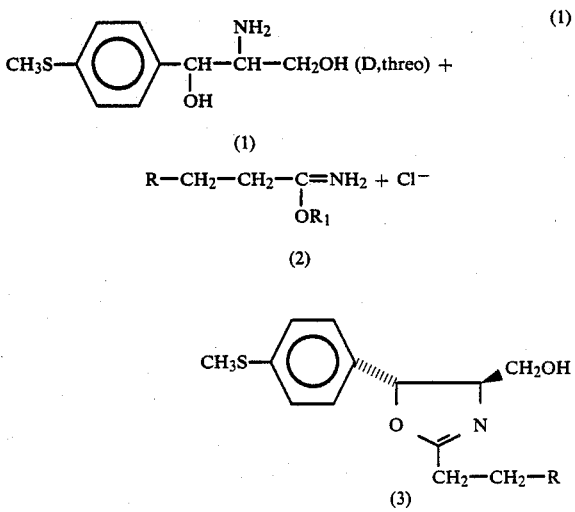

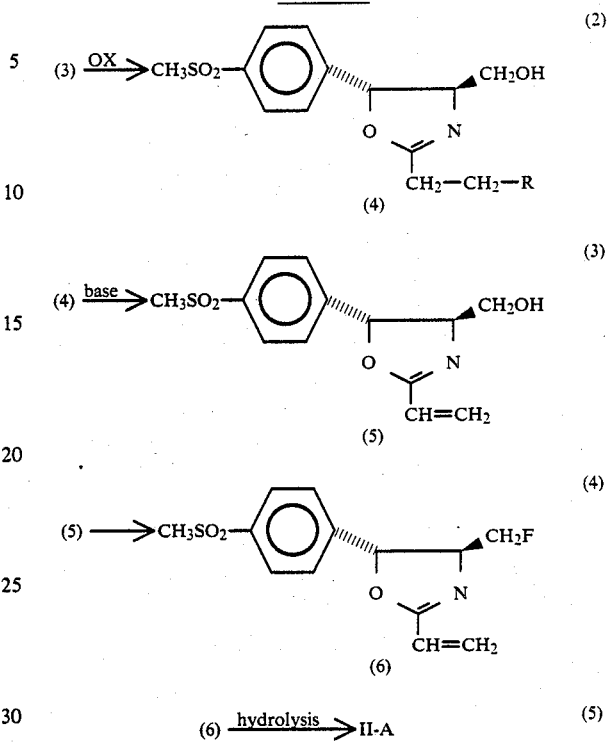

Reaction 1 consists in condensing the 1,3-propanediol derivative (1) with the iminoester (imidate) (2) (R=$C_1C_3$ alcoxy or alkylthio, phenylthio; $R_1$=$CH_3$, $C_2H_5$) or the corresponding nitrile, in order to obtain the oxazoline (3). Compound (2), as far as the process of Scheme 1 is concerned, is a precursor of acrylic acid. In fact the carbon atom in position 2 of the 1,3-oxazoline (3) and the group $CH_2$—$CH_2$—R bonded to it, at the end of the process constitute the N-acryloyl group.

In reaction 2, then, the oxidation to $CH_3SO_2$ group is performed in order to obtain the oxazoline (4).

The oxidation can be carried out with hydrogen peroxide in the presence of catalysts such as sodium tungstate or with peracids in a suitable inert solvent.

The treatment of the oxazoline (4) (reaction 3) with a strong base, for example with tertbutoxide DABCO, DBU or fluoride ion, or with electrophiles like TMS-Cl, $CF_3SO_3Si(CH_3)_3$, or with activated silica or with strong mineral acids, give the 2-vinyloxazoline of formula (5).

The transformation of the hydroxymethyl group in 4 into fluoromethyl follows (reaction 4).

This reaction can be carried out in one step using fluorinating agents, such as FAR or DAST, or in two steps, that is by transforming first the hydroxy into its mesyl-derivative and by reacting this derivative with KF in polyethyleneglycol according to what is described in European Patent Application. No. 130633 (Zambon S.p.A.).

The hydrolysis of the so obtained 4-fluoromethyloxazoline (6), carried out by treatment with aqueous acids and then with bases, gives the desired product (II-A).

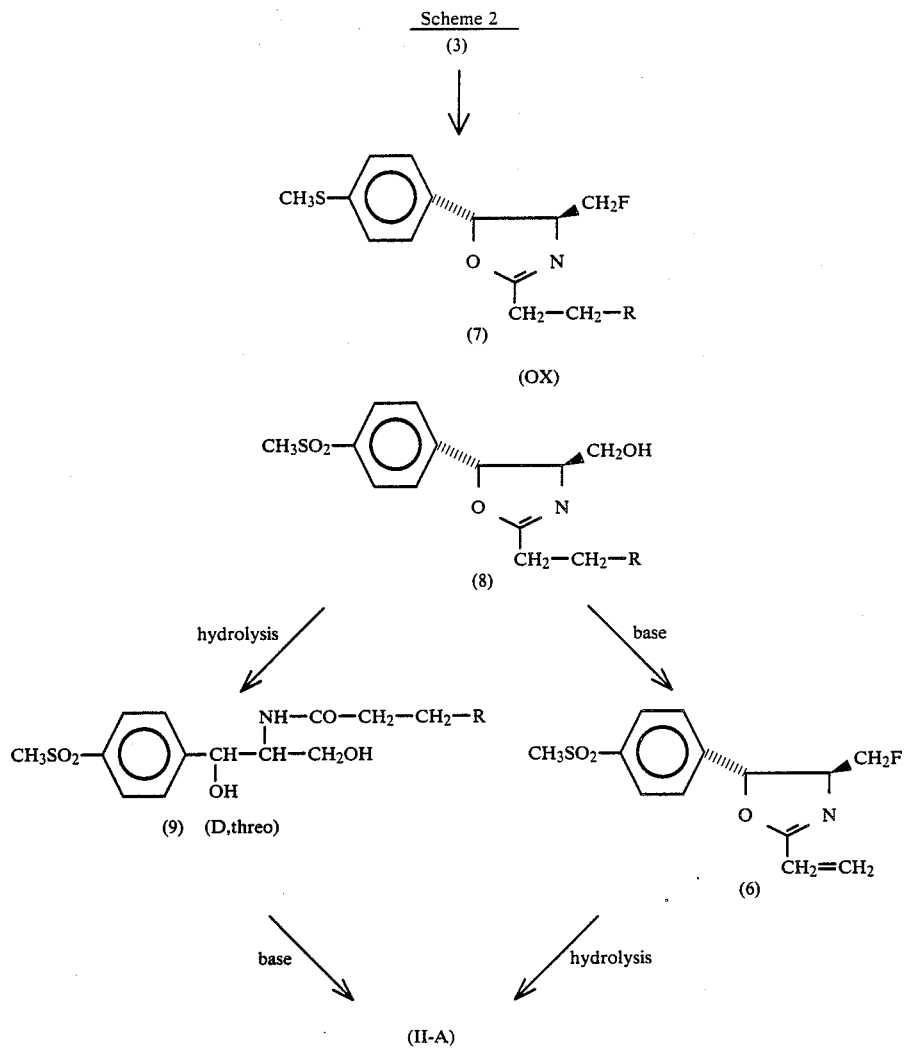

Following the same procedure described for reaction 4 and 2 respectively in Scheme 1, oxazoline (3) (see Scheme 1) is first fluorinated in one or two steps and then oxidized to obtain oxazoline (8).

Compound (8) is treated with a base to give the 2-vinyl-oxazoline of formula (6) which is hydrolyzed according to reaction 5 in Scheme 1.

By inverting the order of reactions, compound (8) is first hydrolyzed to the amide (9) and then treated with a base to obtain compound II-A.

Alternatively oxazoline (6) can be prepared from the corresponding 2-methyl-oxazoline according to the method described by A. I. Meyers et al, J. Org. Chem. 44, 2250 (1979).

The preparation of the esters of formula II starting from compound II-A is carried out according to known methods by using reactive derivatives of the desired acids such as acyl halides or anhydrides.

When it is desired to carry out the esterification with an amino-acid, it is appropriate to protect the amino group for example as N-p.methoxybenzyloxycarbonyl or tertbutyloxycarbonyl derivative.

The salts of the compounds II in which Z is an acyl derived from a dicarboxylic acid or an acyl derived from an aminoacid are prepared in a quite conventional way.

As mentioned above compound II-A and the esters thereof are endowed with an interesting antibiotic activity.

Compound II-A results to be active both "in vitro" and "in vivo" against many gram-positive or gram-negative pathogenous microorganisms and it is also active against those micro-organisms which are resistant to Chloramphenicol and Thiamphenicol. In order to better evaluate the characteristics of compound II-A from a pharmaceutical point of view, studies on therapeutic efficacy, pharmacokinetics and safety have been carried out.

In these studies compound II-A has been compared with compound I-D (according to European Patent No. 14437) from which it differs for the acyl group on the nitrogen (acryloyl instead of dichloroacetyl).

Therapeutic efficacy: it has been evaluated "in vivo" in mice artificially infected with strains of *Salmonella typhimurium* and *Escherichia coli*.

The results, obtained following the method described in example 10, show that the chemotherapeutic action of compound II-A and that of compound I-D are not statistically different.

Pharmacokinetics

In the performed tests it resulted that compound II-A has a pharmacokinetic profile decidedly better than that of compound I-D. Compound II-A, infact, shows a faster absorption by oral route and a faster onset of the hematic active levels.

The maximum of the absorption by oral route has an absolute value (30 ug/ml) which is about 2-3 times higher than that of compound I-D and of Thiamphenicol.

The active concentration of compound II-A in serum is prolonged for a period of time longer than that of compound I-D.

The above pointed out parameters, that is rapidity of absorption, high peak value, protraction of the effective hematic levels, are particularly important factors in relation to antibiotic therapy.

Safety

Compound II-A proved to be an antibiotic endowed with a high safety in therapy. $LD_{50}$ of the product resulted to be higher than 3000 mg/kg.

Furthermore, the compound does not interfere significantly with the mechanisms of mitochondrial proteic synthesis, showing to be without any relevant cytotoxic effect as well.

Another relevant aspect in the safety of an antibiotic is its metabolic resistance.

Compound II-A is resistant to metabolism. It is excreted unchanged in the urine with a percentage higher than that of compound I-D as well as that of Thiamphenicol, both in the experimental animal and in man.

This factor is important also in relation to the use of compound II-A in the disinfection of the urinary tract.

A potential problem related to the use of known antibiotics of the same chemical class is their interference with the mechanisms of spermatogenesis.

In order to verify the influence of compound II-A on spermatogenesis, a study on the fertility of rat was carried out, according to the method described in example 11, in comparison with compound I-D.

From the results of the above study it is possible to conclude that compound II-A is well-tolerated and it does not affect the normal reproductive processes in any way.

Compound I-D, on the contrary, even if it is well-tolerated, negatively affects the reproductive capacities of male and the observations carried out up to 9 weeks from the end of the treatment have not allowed to show reversibility of the effect. In the same test Thiamphenicol shows negative effect on fertility but this effect is reversible after about nine weeks from the end of the treatment.

From the performed tests and from the obtained results it is possible to conclude that the compounds of formula II can be usefully employed in the therapy of bacterial infections in man and in warm-blooded animals.

The treatable infections comprise infections of the respiratory tract, of the gastrointestinal tract, of the uro-genital tract and of external organs such as skin, eyes and ears.

The compounds of formula II are preferably used in a suitable pharmaceutical preparation useful for the administration by oral, parenteral, rectal or topical route.

Such pharmaceutical preparations comprise tablets, capsules, syrups, injectable solutions ready to use or to be prepared at the moment of use by dilution of a freeze-dried, suppositories, solutions, creams, ointments and eye-drops.

For veterinary use, in addition to the above preparations, it is possible to prepare solid or liquid concentrates to be diluted in fodder or poultry feed or in drinking-water.

Depending on the kind of preparation, they may contain, in addition to a therapeutically effective amount of one or more compounds of formula II, solid or liquid excipients and diluents for pharmaceutical or veterinary use and, optionally, other usual additives such as thickening agents, aggregating agents, lubricants, disintegrants, flavouring agents and colouring agents.

In order to fight particular infections, an effective amount of another antibiotic with a complementary effect may be associated with the compound of formula II.

The effective amount of compound of formula II can vary in relation to different factors such as the seriousness and the stage of the infection, the enjured organ or system, the characteristics of the host, the susceptibility of the bacterial species responsible for the infection, the selected administration route.

The therapeutic dosage, referring to compound II-A, will be generally between 5 and 500 mg/kg body weight/day and will be administered in a single dose or in severl doses at appropriate intervals.

In order to better illustrate the invention the following examples are given.

EXAMPLE 1

N-[(1S,2R)-1-(fluoromethyl-2-hydroxy-2-(4-methylsulphonylphenyl)-ethyl]-2-propenamide. (II-A)

A solution of acryloyl chloride (33.18 g, 0.366 moles) in methylene chloride (336 ml) is added dropwise separately and contemporaneously with NaOH 1N (366 ml) to a solution, cooled at 0° C, of (1R,2S)-2-amino-3-fluoro-1-(4-methylsulphonylphenyl)-1-propanol hydrochloride (80 g, 0.282 moles) in methylene chloride (2050 ml) and NaOH 1N (282 ml) keeping the pH value at about 9 and the temperature below +5° C.

At the end of the addition the reaction mixture is kept under stirring for 30 minutes at 0° C. and then for 1 hour at room temperature, keeping the pH at about 9 and adding further NaOH 1N if necessary.

Then tetrahydrofuran (THF) (2500 ml) is added and the layers are separated. The aqueous phase is extracted again with THF and the organic extracts are washed successively with water, HCl 5%, water, aqueous NaHCO$_3$ and then with water again.

After drying, evaporation of the solvent under reduced pressure and treatment of the residue with methyl-tertbutyl-ether, a crude crystal product (61.6 g) is obtained.

The crude is purified by crystallization from a mixture of acetonitrile and methyl-tertbutyl-ether in the ratio 4:1.

The desired compound (56 g) is obtained as a crystalline solid (m.p. 180°-18° C.). $[\alpha]_D^{20} = -6.2°$ (c=1, DMF)

$^1$H NMR (60 MHz, DMSO-d$_6$) delta (ppm): 7.82 [q (dd), 4H, aromatics]; 6.6-5.4 (m, 3H, vinyl); 5.2-3.8 (m, 4H, CH—CH—CH$_2$); 3.20 (s, 3H, CH$_3$SO$_2$).

IR (KBr) meaningful bands at 3500, 3360, 1650, 1505, 1400, 1290 and 1155 (cm$^{-1}$)

U.V. ($\lambda_{max}$MeOH,nm): 272 (log $\epsilon$=2.93); 224 (log $\epsilon$=4.24).

EXAMPLE 2

N-[(1S,2R)-2-acetoxy-1-fluoromethyl-2-(4-methylsulphonyl)-ethyl]-2-propenamide.

To a suspension of N-[(1S,2R)-1-fluoromethyl-2-hydroxy-2-(4-methylsulphonylphenyl)-ethyl]-2-propenamide (II-A) (1.5 g, 5 mmoles), prepared according to the method described in example 1, in acetonitrile (30 ml) containing triethylamine (2.1 ml, 15 mmoles), acetic anhydride (1.06 ml, 10 mmoles) is added rapidly at room temperature.

After 3 hours the reaction mixture is concentrated under reduced pressure and the residue is treated with dichloromethane and water.

The organic phase is separated and the aqueous phase is extracted again with dichloromethane.

The organic extracts, after drying on sodium sulphate and evaporation of the solent give an amorphous crude (1.65 g). The crude is purified by chromatography on silica gel (200 g) (eluenet dichloromethane:methanol=95:5).

The desired compound (1.2 g) is obtained as an amorphous solid (m.p. 66°–70° C.).

$[\alpha]_D^{20} = -20.9°$ (c=1, DMF)

$^1$H NMR (60 MHz, DMSO-d$_6$) delta (ppm): 7.9 (dd, 4H, aromatics); 6.7–5.5 (m, 4H, CH—O+vinyl); 5.1–3.8 (m, 3H, CH—CH$_2$F); 3.3 (s, 3H, CH$_3$SO$_2$); 2.15 (s, 3H, CH$_3$COO).

IR (KBr) meaningful bands at 1750, 1670, 1540, 1310, 1160 (cm$^{-1}$)

U.V. ($\lambda_{max}$MeOH,nm):276 (log $\epsilon$=4.31).

EXAMPLE 3

(1R,2S)-3-fluoro-2-propenamido-1-(4-methylsulphonylphenyl)-1-propyl hemisuccinate sodium salt.

A suspension of N-[(1S,2R)-1-fluoromethyl-2-hydroxy-2-(4-methylsulphonylphenyl)-ethyl]-2-propenamide (II-A) (3.2 g; 10.6 mmoles), prepared according to the method described in example 1, in acetonitrile (64 ml) is heated at 50° C. for 20 minutes.

The suspension is, then, cooled at 0° C., and triethylamine (2.95 ml, 21.2 mmoles) and succinic anhydride (1.59 g, 15.9 mmoles) are added to it.

The temperature is let to rise up to 20° C. and after 15 hours the solution is evaporated to dryness under reduced pressure.

The residue is treated with dichloromethane and the solution is washed with diluted HCl and, then, with water.

After drying on sodium sulphate and evaporation of the solvent an amorphous crude (2.15 g) is obtained.

This crude is purified by chromatography on silica gel (300 g) (eluent dichloromethane:methanol:acetic acid=89:10:1).

A pure compound (1.24 g) is obtained; it is suspended in water, treated with a stoichiometric amount of sodium bicarbonate and stirred in order to have a complete solubilization. The solution is filtered and evaporated under reduced pressure giving the desired compound as an amorphous solid.

$^1$H NMR (60 MHz, DMSO-d$_6$) delta (ppm): 7.9 (dd, 4H, aromatics); 6.8–5.5 (m, 4H, vinyl and CH—O—CO); 5.1–4.0 (m, 3H, CH—CH$_2$F); 3.2 (s, 3H, CH$_3$); 2.8–2.3 (m, 4H, CH$_2$—CH$_2$).

IR (KBr) meaningful bands at 1735, 1660, 1580, 1410, 1300, 1150 (cm$^{-1}$).

U.V. ($\lambda_{max}$MeOH,nm):223 (log $\epsilon$=4.24)

The following examples show alternative procedures for the preparation of compound II-A.

EXAMPLE 4

(4R,5R)-4-hydroxymethyl-2-(2-isopropoxyethyl)-5-(4-methylthiophenyl)-2-oxazoline (compound A)

(1R,2R)-2-amino-3-(4-methylthiophenyl)-1,3-propanediol (160 g, 0.75 moles) is added to a suspension of methyl 3-propyloxypropanimidate hydrochloride (160 g, 0.88 moles) in dichloromethane (790 ml) and the reaction mixture is stirred at room temperature for 18 hours.

Water (500 ml) is added and the layers are separated.

The aqueous phase is extracted twice again with dichloromethane.

The organic extracts are collected, washed with water, dried on sodium sulphate and evaporated to dryness under reduced pressure.

An oil (172 g), which then solidifies, is obtained.

The solid crude is purified by crystallization from a mixture of methyl-tertbutyl-ether and hexane in the ratio 1:1 (500 ml).

The desired product (compound A) is obtained as a crystalline solid (96.3 g).

(m.p. 68°–70° C.)

$[\alpha]_D^{20} = +71.8°$ (c=1, DMF)

$^1$H NMR (60 MHz, DMSO-d$_6$) delta (ppm): 7.3 (s, 4H, aromatics); 4.3–3.5 [m, 5H, CH—CH—CH$_2$O+CH(CH$_3$)$_2$]; 2.7 (t, 2H, CH$_2$—CH$_2$); 2.5 (s, 3H, CH$_3$S); 1.2 [d, 6H, (CH$_3$)$_2$CH].

IR (KBr) meaningful bands at 3215, 1660, 1330, 1090, (cm$^{-1}$)

U.V. ($\lambda_{max}$MeOH,nm): 260 (log $\epsilon$=4.21).

EXAMPLE 5

(4S,5R)-4-fluoromethyl-2-(2-isopropoxyethyl)-5-(4-methylthiophenyl)-2-oxazoline (compound B).

A solution of compound A (3.70 g, 12 mmoles), prepared as described in example 4, in THF (20 ml) is added dropwise to a solution of diethylaminosulphurtrifluoride (DAST) (2 ml, 15.6 mmoles) in anhydrous THF (20 ml) kept under nitrogen at 10° C.

After 24 hours under stirring at room temperature, the reaction mixture is poured into an aqueous saturated solution of sodium bicarbonate and is extracted several times with ethyl acetate. The organic extracts are collected, washed with water, dried on sodium sulphate and evaporated to dryness under reduced pressure. A crude (4 g) is obtained and is purified by chromatography on silica gel (eluent petroleum ether:ethyl acetate=1:1).

The desired compound B is obtained as an oil (1.3 g).

$[\alpha]_D^{20} = -9.3°$ (c=1, DMF)

$^1$H NMR (60 MHz, CDCl$_3$) delta (ppm): 7.3 (s, 4H, aromatics); 5.35 (d, 1H, CH—O); 5.0–3.4 [m, 6H, CH$_2$CH$_2$F+CH(CH$_3$)$_2$+CH$_2$—CH$_2$]; 2.70 (t, 2H, CH$_2$CH$_2$); 2.50 (s, 3H, CH$_3$S); 1.2 [d, 6H, (CH$_3$)$_2$CH]

IR (nujol) meaningful bands at 1640, 1540 (cm$^{-1}$)

U.V. ($\lambda_{max}$MeOH,nm): 2.58 (log $\epsilon$=4.15).

EXAMPLE 6

(4S,5R)-4-fluoromethyl-2-(2-isopropoxyethyl-5-(4-methylthiophenyl)-2-oxazoline (compound B) (see example 5).

Methanesulphonyl chloride (1.26 g, 11 mmoles) is added to a solution of compound A (3.1 g, 10 mmoles), prepared as described in example 4, in pyridine (12 ml) keeping the temperature at 0° C.

After 4 hours the reaction mixture is poured into water and ice and is extracted with ethyl acetate.

The organic extracts are, then, washed rapidly with very diluted HCl and with water, are dried on sodium sulphate and evaporated under reduced pressure.

The crude product is purified by chromatography on silica gel (eluent dichloromethane:methanol=97:3).

The compound (4R,5R)-2-(2-isopropoxyethyl)-4-methansulphonylmethyl-5-(4-methylthiophenyl)-2-oxazoline is obtained as an oil (1.7 g).

$^1$H NMR (60 MHz, CDCl$_3$) delta (ppm): 7.3 (s, 4H, aromatics); 5.3 (d, 1H, CH—O); 4.6-3.4 [m, 6H, =N—CH—CH$_2$—OSO$_2$+CH$_2$—CH$_2$+CH(CH$_3$)$_2$]; 3.1 (s, 3H, CH$_3$SO$_2$O); 2.7 (t, 2H, CH$_2$CH$_2$); 2.5 (s, 3H, CH$_3$S); 1.2 [d, 6H, (CH$_3$)$_2$CH].

A mixture of this oil (1.2 g, 3 mmoles) and potassium fluoride (0.87 g, 15 mmoles) in tetraethylene glycol (10 ml) is heated at 95° C. for 27 hours.

The reaction mixture is poured into water (200 ml) and is extracted several times with dichloromethane. The organic extracts are collected, washed twice with water, dried on sodium sulphate and evaporated.

The crude (0.9 g) is purified by chromatography on silica gel (110 g) (eluent petroleum ether:ethyl acetate=1:1).

The desired compound B (0.2 g), with the same characteristics of that obtained with the method described in example 5, is obtained.

EXAMPLE 7

(4S,5R)-4-fluoromethyl-2-(2-isopropoxyethyl)-5-(4-methylsulphonylphenyl)-2-oxazoline (compound C).

A solution of m.chloroperbenzoic acid (1.88 g, 9.23 mmoles, titre 85%) in dichloromethane (20 ml) is added dropwise to a solution of compound B (0.82 g, 2.63 mmoles), prepared as described in example 5 or 6, cooled at 0° C., in dichloromethane (20 ml).

After an hour at 0° C., the reaction mixture is treated with an aqueous solution of sodium bicarbonate at 5%, the layers are separated and the aqueous phase is extracted again. The organic extracts are washed, dried and concentrated giving a semi-solid crude (1.5 g) which is purified by chromatography on silica gel (eluent dichloromethane:methanol=95:5).

A crystalline product (compound C-0.3 g) is obtained.

(m.p. 80°-82° C.)

$[\alpha]_D^{20} = +31.5°$ (c=1, DMF)

$^1$H NMR (60 MHz, DMSO-d$_6$) delta (ppm): 7.9 (dd, 4H, aromatics); 5.6 (d, 1H, CH—O); 5.0-4.1 (m, 3H, CH—CH$_2$F); 4.1-3.4 [m, 3H, CH(CH$_3$)$_2$+CH$_2$—CH$_2$]; 3.2 (s, 3H, CH$_3$SO$_2$); 2.6 (t, 2H, CH$_2$CH$_2$); 1.1 [d, 6H, (CH$_3$)$_2$CH].

IR (KBr) meaningful bands at 1675, 1305, 1145 (cm$^{-1}$)

U.V. ($\lambda_{max}$ MeOH,nm): 224 (log $\epsilon$=4.17).

EXAMPLE 8

N-[(1S,2R)-1-fluoromethyl-2-hydroxy-2-(4-methylsulphonylphenyl)-ethyl]-3-isopropoxy-propanamide (compound D).

Perchloric acid 1N (1 ml, 1 mmole) is added slowly to a suspension of compound C (343 mg, 1 mmole), prepared as described in example 7, in water (3.5 ml).

The reaction mixture is stirred in order to have a complete solubilization and is poured into an aqueous solution of sodium bicarbonate at 5%. After adding sodium chloride, the mixture is extracted with THF several times. The organic extracts are dried on sodium sulphate and evaporated under educed pressure giving a crude oil which is purified by chromatography on silica gel (eluent dichloromethane:methanol=9:1).

A crystalline product (compound D - 0.33 g) is obtained. (m.p. 83°-85° C.)

$[\alpha]_D^{20} = -12.9°$ (c=1, DMF)

$^1$H-NMR (60 MHz, DMSO-d$_6$) delta (ppm): 7.8 (dd, 4H, aromatics); 5.1-3.7 (m, 4H, CH—CH—CH$_2$F); 3.7-3.2 [m, 3H, CH(CH$_3$)$_2$+CH$_2$—CH$_2$]; 3.2 (s, 3H, CH$_3$SO$_2$); 2.3 (t, 2H, CH$_2$CH$_2$); 1.0 [d, 6H, (CH$_3$)$_2$CH]

IR (KBr) meaningful bands at 3380, 1655, 1530, 1300, 1150 (cm$^{-1}$)

U.V. ($\lambda_{max}$MeOH,nm): 225 (log $\epsilon$=4.36).

Compound D was obtained also from compound B (see example 5) by oxidation with hydrogen peroxide and acetic anhydride.

By treatment of compound D with potassium tert-butoxide in THF a crude is obtained from which compound II-A, with the same characteristics of that described in example 1, is separated by chromatography.

EXAMPLE 9

(4S,5R)-4-fluoromethyl-5-(4-methylsulphonylphenyl)-2-vinyl-2-oxazoline (compound E).

Compound C (6.87 g, 0.02 moles), prepared as described in example 7, is added to a solution of potassium tertbutoxide (22.44 g, 0.2 moles) in anhydrous THF (420 ml), kept at −80° C. under nitrogen. After 10 minutes at −80° C., phosphate buffer (pH 6) is added, the cooling is taken off and the reaction mixture is diluted with salt water (NaCl).

The organic phase is separated and the aqueous phase is extracted again with THF.

The organic extracts are collected, dried and evaporated to dryness. The crude oil is purified by chromatography on silica gel (eluent dichloromethane:methanol=98.2) giving compound E (2.8 g) as an oil.

$^1$H NMR (60 MHz, CDCl$_3$) delta (ppm): 7.9 (dd, 4H, aromatics); 6.6-5.5 (m, 4H, CH—O+vinyl); 5.3-4.1 (m, 3H, CH—CH$_2$F); 3.1 (s, 3H, CH$_3$SO$_2$).

By operating in a way similar to that described in example 8, the hydrolysis of compound E gave a crude from which compound II-A, with the same characteristics of that described in example 1, is separated by chromatography.

EXAMPLE 10

"In vivo" therapeutic activity.

The therapeutic activity of compound II-A was evaluated in comparison with that of compound I-D, by experimental infection in mouse.

In this experiment albino mice—stock CD/1—with a body weight between 19 and 21 g were used. The mice were stalled and fed with a standard diet and water "ad libitum".

The evaluation of the average protective dose ($PD_{50}$) of the two products was carried out after infection by *Salmonella typhimurium* and by *Escherichia coli*.

The animals, in a number of 140 each infection, were divided into 14 groups of 10 mice each and they were infected by peritoneal route with 0.25 ml of a suspension of the strain under test, corresponding to a dose 100 times higher than the $LD_{50}$.

After an hour from the infection the animals of 6 groups have received different doses, increasing with geometrical progression, of compound II-A by oral route, while the animals of other 6 groups have received the same treatment with equivalent amounts of compound I-D. The remaining two groups were used as control infected and not treated.

The administration of the above compounds were carried out twice a day for three days and the observation of the animals was prolonged for a period of 5 days.

The determination of $PD_{50}$ of the two compounds and the evaluation of a possible significant difference between the values was carried out according to Litchfield and Wilcoxon. [J. Pharmacol. Exper. Therap. 96, 99–113, (1949)]

The chemotherapeutic action of compound II-A in the experimental infection by *Salmonella typhimurium* and by *Escherichia coli* has resulted to be nearly overlapped and statistically not different with respect to the action exploited, under the same experimental conditions, by compound I-D.

EXAMPLE 11

Effect on spermatogenesis.

A study was carried out in order to evaluate the possible effects on the reproductive function, in male rat, of the following compounds: Thiamphenicol, I-D and II-A.

The study was carried out according to the below reported procedure:
Animal species: CD(SD)BR Charles River Rat
Administration route: oral
Administration frequency: every day for 4 weeks
Administered amount of compound: 0.28 mM/kg body weight/day
Administration volume: 10 ml/kg body weight
Control: gum-arabic at 2%
Male animal, casually allotted to the following groups:
1. Control
2. Treatment with Thiamphenicol
3. Treatment with compound I-D
4. Treatment with compound II-A The examination of the reproductive function was performed by mating the male animals with not treated females during the 1st, 4th, 6th and 9th week from the end of the treatment.

The result of conception was examined in the female animals after 2 weeks from the mating.

Some of the male animals were sacrificed at the end of the treatment and the other ones at the end of the matings. During the autopsies the organs of the reproductive apparatus were isolated and afterwards they underwent a hystological examination.

The check of fertility of the treated male animals, carried out by mating with untreated females, showed different results in relation to the compounds of the treatment and to the period of check.

During the week immediately after the end of the treatment, every group showed a normal index of fertility.

In the checks carried out during the fourth and the sixth week from the end of the treatments a remarkable negative action on the fertility of male animals was noted for Thiamphenicol and compound I-D.

In the last cycle of mating, carried out at 65–70 days from the end of the treatments, the males treated with Thiamphenicol showed a normal index of fertility, while the males treated with compound I-D showed an index of fertility still lower than usual values.

The male animals treated with compound II-A, according to the present invention, showed a normal index of fertility in every cycle of mating.

The administration of the three considered compounds never affected the normal mating of rats.

In the groups characterized by an unsatisfactory index of fertility, that is treated with Thiamphenicol or with compound I-D, most of the few pregnant females showed, in autopsy, a number of "corpi lutei", and consequently of embryos, lower than the normal values that may be found in the used rat colony.

This phenomenon leads to the conclusion that, likely, also in fertile male animals, during the period of study, the number of morphologically and functionally normal spermatozoa present in sperm was relatively low.

The absolute weight of testicles, at the end of the treatment and of the cycles of mating, resulted to be statistically lower than that of control animals for the group treated with compound I-D.

The analysis of the data concerning the ratio between weight of testicles and body weight evidenced a significant decrease only as far as the group of animals treated with compound I-D is concerned and only at the end of the matings.

Therefore, it is possible to conclude that, under the performed experimental conditions:

Thiamphenicol negatively affects, in rat, the index of fertility; the phenomenon is, however, completely reversible after nine weeks from the end of the treatment;

compound I-D is well-tolerated, but it may affect negatively on the reproductive capacities of male animals; the observations carried out up to nine weeks from the end of the treatment do not allow to verify the reversibility of the phenomenon;

compound II-A is well-tolerated in rat and it does not affect in any way the normal reproductive processes.

What we claim is:

1. A compound of formula

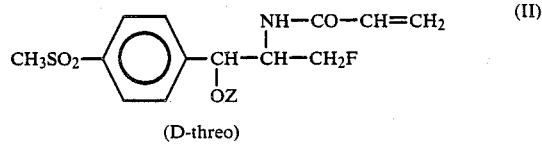

(D-threo)

wherein:

Z represents a hydrogen atom or represents an optionally substituted acyl group derived from a saturated or unsaturated aliphatic, aromatic or arylaliphatic acid having up to 16 carbon atoms, from an aliphatic or aromatic dicarboxylic acid having up to 12 carbon atoms, or from a natural aminoacid;

and, when Z is an acyl of a dicarboxylic acid or of an amino-acid, the corresponding pharmaceutically acceptable salts with bases or with acids respectively.

2. The compound, according to claim 1, N-[(1S,2R)-1-fluoromethyl-2-hydroxy-2-(4-methylsulphonyl-phenyl)-ethyl]-2-propenamide.

3. A pharmaceutical composition with antibiotic acitivity for human or veterinary use containing as active ingredient an effective amount of a compound according to claim 1, together with a pharmaceutically acceptable inert carrier.

4. A method for the treatment of bacterial infections in man and warm-blooded animals consisting of administering to the subject a therapeutically effective amount of a compound according to claim 1.

* * * * *